(12) United States Patent
Jones et al.

(10) Patent No.: US 11,571,224 B2
(45) Date of Patent: Feb. 7, 2023

(54) TIBIAL CUT GUIDE

(71) Applicant: Zimmer, Inc., Warsaw, IN (US)

(72) Inventors: Nolan C. Jones, Warsaw, IN (US); Richard Moore, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 476 days.

(21) Appl. No.: 16/698,509

(22) Filed: Nov. 27, 2019

(65) Prior Publication Data

US 2020/0093502 A1    Mar. 26, 2020

Related U.S. Application Data

(62) Division of application No. 15/467,663, filed on Mar. 23, 2017, now Pat. No. 10,517,616.

(60) Provisional application No. 62/312,808, filed on Mar. 24, 2016.

(51) Int. Cl.
| | | |
|---|---|---|
| *A61B 17/17* | (2006.01) | |
| *A61F 2/38* | (2006.01) | |
| *A61B 17/15* | (2006.01) | |
| *A61B 17/16* | (2006.01) | |

(52) U.S. Cl.
CPC ........ *A61B 17/1764* (2013.01); *A61B 17/157* (2013.01); *A61B 17/1675* (2013.01); *A61F 2/389* (2013.01); *A61F 2/3859* (2013.01)

(58) Field of Classification Search
CPC ..... A61B 17/17; A61B 17/1764; A61B 17/16; A61B 17/1675; A61F 2/38; A61F 2/389
See application file for complete search history.

(56) References Cited

U.S. PATENT DOCUMENTS

| | | | | |
|---|---|---|---|---|
| 5,597,379 | A | * | 1/1997 | Haines ............... A61B 17/1764 606/88 |
| 10,517,616 | B2 | * | 12/2019 | Jones ................. A61B 17/1675 |
| 2008/0243127 | A1 | | 10/2008 | Lang et al. |

(Continued)

FOREIGN PATENT DOCUMENTS

| | | |
|---|---|---|
| WO | WO-2012024306 A2 | 2/2012 |
| WO | WO-2012051542 A2 | 4/2012 |
| WO | WO-2017165653 A1 | 9/2017 |

OTHER PUBLICATIONS

U.S. Appl. No. 15/467,663, filed Mar. 23, 2017, Tibial Cut Guide.

(Continued)

*Primary Examiner* — Christopher J Beccia
(74) *Attorney, Agent, or Firm* — Schwegman Lundberg & Woessner, P.A.

(57) ABSTRACT

Methods and apparatuses including apparatuses that can be used for guiding resection of a tibia during a knee replacement surgery procedures are disclosed. According to one example, an apparatus for guiding a tibial bone cut during knee replacement surgery is disclosed. The apparatus can comprise a first portion and a second portion. The first portion can be configured to position the apparatus relative to one or more of a medial condyle of a femur, a lateral condyle of the femur, a medial condyle of a femoral component and a lateral condyle of the femoral component. The second portion can be connected to the first portion and can define one or more slots. The slots can be configured for at least one of a first proximal cut and a first sagittal cut to the tibia.

20 Claims, 12 Drawing Sheets

(56) References Cited

U.S. PATENT DOCUMENTS

| | | | |
|---|---|---|---|
| 2009/0043310 A1* | 2/2009 | Rasmussen | A61B 17/1764 606/88 |
| 2009/0087276 A1 | 4/2009 | Rose | |
| 2010/0121334 A1 | 5/2010 | Couture et al. | |
| 2014/0066720 A1* | 3/2014 | Wilkinson | A61B 17/02 606/88 |
| 2015/0190144 A1* | 7/2015 | Kennedy | A61B 17/157 606/88 |
| 2016/0199077 A1* | 7/2016 | Dungy | A61B 17/155 606/88 |
| 2017/0273696 A1 | 9/2017 | Jones et al. | |

OTHER PUBLICATIONS

"European Application Serial No. 17715610.6, Communication Pursuant to Article 94(3) EPC dated May 6, 2020", 6 pgs.

"European Application Serial No. 17715610.6, Response filed Sep. 15, 2020 to Communication Pursuant to Article 94(3) EPC dated May 6, 2020", 29 pgs.

"U.S. Appl. No. 15/467,663, Non Final Office Action dated Apr. 26, 2019", 8 pgs.

"U.S. Appl. No. 15/467,663, Notice of Allowance dated Aug. 26, 2019", 6 pgs.

"U.S. Appl. No. 15/467,663, Response filed Feb. 7, 2019 to Restriction Requirement dated Dec. 19, 2018", 7 pgs.

"U.S. Appl. No. 15/467,663, Response filed Jul. 24, 2019 to Non-Final Office Action dated Apr. 26, 2019", 14 pgs.

"U.S. Appl. No. 15/467,663, Restriction Requirement dated Dec. 19, 2018", 7 pgs.

"European Application Serial No. 17715610.6, Response filed May 17, 2019 to Office Action dated Nov. 7, 2018", 19 pgs.

"International Application Serial No. PCT/US2017/023826, International Preliminary Report on Patentability dated Oct. 4, 2018", 9 pgs.

"International Application Serial No. PCT/US2017/023826, International Search Report dated Jul. 19, 2017", 7 pgs.

"International Application Serial No. PCT/US2017/023826, Invitation to Pay Additional Fees and Partial Search Report dated May 26, 2017", 14 pgs.

"International Application Serial No. PCT/US2017/023826, Written Opinion dated Jul. 19, 2017", 9 pgs.

* cited by examiner

TIBIAL CUT GUIDE

CLAIM OF PRIORITY

This application is a divisional of U.S. patent application Ser. No. 15/467,663, filed on Mar. 23, 2017, which claims the benefit of U.S. Provisional Patent Application Ser. No. 62/312,808, filed on Mar. 24, 2016, the benefit of priority of each of which is claimed hereby, and each of which is incorporated by reference herein in its entirety.

FIELD

The present subject matter relates to orthopedic procedures and, more particularly, to bone resection apparatuses and methods for performing knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral component implanted on the distal end of the femur, which articulates with a tibial component implanted on the proximal end of a tibia to replicate the function of a healthy natural knee. Various types of arthroplasties are known including a total knee arthroplasty, where all of the articulating compartments of the joint are repaired with prosthetic components, and a unicompartmental knee arthroplasty, where only one damaged compartment of the knee is repaired with prosthetic components.

OVERVIEW

The present inventor recognizes, among other things, an opportunity for reducing surgical error and surgical complexity. More particularly, the present inventor has recognized that in a bi-cruciate preserving knee arthroplasty a total femoral component can be used with two independent unicompartmental tibial implants or with two independent bearing components connected together with a bridge shaped tray. Such arrangement, however, can require the surgeon to determine a proper spacing for the tibial components such that they articulate properly with the femoral component and are arranged in a desired manner on the resected tibia. Mismatch or error in spacing the tibia components can result in high rates of wear and/or loading that may result in component loosening or other complications. Another challenge of the bi-cruciate preserving arthroplasty is failing to maintain a minimum joint spacing between the lateral compartment and the medial compartment can result in increased chance of an ACL tear. In view of the foregoing, the present inventor proposes exemplary cut guides that can attach to the femoral component to better reference a medial-lateral geometry of the femoral component. The cut guides can include at least one sagittal capture for sagittal resection(s) of the tibia so that the tibial implant(s) can be positioned with a desired bearing(s) spacing and with a desired medial-lateral position that can optimize articulation between the femoral component and the tibial components so as to reduce the likelihood of wear and other complications. Thus, the present inventor has recognized that surgical complexity can be reduced by providing cut guides with a sagittal capture and/or transverse capture that predefines a cut medial-lateral relative to one or more articulating surfaces of the femoral component. According to further examples, the present inventor recognize that the cut guide can be configured to provide the surgeon with various movement options including translation proximal-distal to achieve a desired sagittal cut depth, translation medial-lateral as patient geometry dictates and rotation such as to accommodate various degrees of flexion so the surgeon can set the cut guide in an appropriate location relative to the tibia so that resections can be performed in desired locations. Further examples of the cut guide may not connect to the femoral component to mount the cut guide thereto but instead can have one or more members that reference articular surface(s) of the femoral component and/or the femur.

To further illustrate the apparatuses and methods disclosed herein, the following non-limiting examples are provided:

Example 1 is an apparatus for guiding resection of a tibia during a knee replacement surgery, the apparatus can comprise: a first portion configured to position the apparatus relative to one or more of a medial condyle of a femur, a lateral condyle of the femur, a medial condyle of a femoral component and a lateral condyle of the femoral component; and a second portion connected to the first portion and defining one or more slots, the slots configured for at least one of a first proximal cut and a first sagittal cut to the tibia.

In Example 2, the subject matter of Example 1 optionally includes at least one aperture disposed between the first of the one or more slots for the first sagittal cut and the second of the one or more slots for the first proximal cut, the aperture is configured to receive one of a stop component or fixation component therein.

In Example 3, the subject matter of any one or more of Examples 1-2 optionally includes wherein the one or more slots are configured to define a first medial-lateral cut length such that the first proximal cut is to a first single compartment of the tibia.

In Example 4, the subject matter of Example 3 optionally includes wherein the one or more slots are configured to define a second medial-lateral cut length spaced from the first medial-lateral cut length by an intercondylar portion such that a second proximal cut is to a second single compartment of the tibia.

In Example 5, the subject matter of Example 4 optionally includes wherein the one or more slots are configured to define the first sagittal cut on a first side of the intercondylar portion and a second sagittal cut on a second side of the intercondylar portion.

In Example 6, the subject matter of Example 5 optionally includes wherein the first sagittal cut is canted at an acute angle relative to the second sagittal cut.

In Example 7, the subject matter of any one or more of Examples 1-6 optionally includes wherein the first portion is configured to connect to one or both of the medial condyle of the femoral component and the lateral condyle of the femoral component.

In Example 8, the subject matter of any one or more of Examples 1-7 optionally includes wherein the first portion comprises: a first arm having a first male connection feature configured to connect with a first female connection feature in the medial condyle of the femoral component; a second arm having a second male connection feature configured to connect with a second female connection feature in the lateral condyle of the femoral component; and an intermediate portion connected to the first arm and the second arm at a proximal end portion and connected to the second portion at a distal end portion.

In Example 9, the subject matter of any one or more of Examples 1-8 optionally includes wherein apparatus includes one or more adjustment mechanisms to adjust a position of the second portion in one or more of rotation, a proximal-distal direction and a medial-lateral position.

In Example 10, the subject matter of Example 9 optionally includes wherein the one or more adjustment mechanisms comprise at least one of a proximal-distal translation mechanism, a medial-lateral translation mechanism, an extension plane rotation mechanism and an external rotation mechanism.

In Example 11, the subject matter of any one or more of Examples 1-10 optionally includes wherein the femoral component comprises a total femoral component and includes a first slot in the medial condyle configured to receive a medial end of the first portion therein and a second slot in a lateral condyle configured to receive a lateral end of the first portion therein, the first and second slots configured to facilitate orientation of the first portion in a desired position relative to the femoral component.

Example 12 is an apparatus for guiding resection of a tibia during a bicompartmental knee replacement surgery, the apparatus can comprise: a first portion configured to connect to a medial condyle of a femoral component and configured to connect to a lateral condyle of the femoral component; and a second portion connected to the first portion and defining a plurality of slots configured for at least a first proximal cut, a first sagittal cut, a second proximal cut, and a second sagittal cut to the tibia, the slots are configured to define a first medial-lateral cut length such that the first proximal cut is to a first single compartment of the tibia and are configured to define a second medial-lateral cut length such that the second proximal cut is to a second single compartment of the tibia.

In Example 13, the subject matter of Example 12 optionally includes at least one aperture disposed between one of the plurality of slots for the first sagittal cut and another of the plurality of slots for the first proximal cut, the aperture is configured to receive one of a stop component or fixation component therein.

In Example 14, the subject matter of any one or more of Examples 12-13 optionally include and 13, wherein the second medial-lateral cut length is spaced from the first medial-lateral cut length by an intercondylar portion and the slots are configured to define the first sagittal cut on a first side of the intercondylar portion and a second sagittal cut on a second side of the intercondylar portion.

In Example 15, the subject matter of Example 14 optionally includes wherein the first sagittal cut is canted at an acute angle relative to the second sagittal cut.

In Example 16, the subject matter of any one or more of Examples 12-15 optionally includes wherein apparatus includes one or more adjustment mechanisms to adjust a position of the second portion in one or more of rotation, a proximal-distal direction and a medial-lateral position.

In Example 17, the subject matter of any one or more of Examples 12-16 optionally includes further comprising a femoral component that comprises a total femoral component.

Example 18 is a method of performing a tibial knee resection comprising: connecting a cut guide to a femoral component mounted to a resected femur of a patient, the cut guide having slots configured to facilitate at least one of a first proximal cut and a first sagittal cut; and resecting one or more compartments of the tibia by performing one or both of the proximal cut and the sagittal cut utilizing the cut guide.

In Example 19, the subject matter of Example 18 optionally includes adjusting a position of the cut guide relative to the femoral component and the tibia with reference to at least one or more anatomical landmarks of the tibia.

In Example 20, the subject matter of Example undefined optionally includes wherein the anatomical landmarks include one or more of the intercondylar eminence of the tibia, a connection position of an ACL with the tibia, a medial third of a tubercle at insertion of a PCL, and an intercondylar geometry of a femur.

In Example 21, the subject matter of any one or more of Examples 18-20 optionally include wherein the cut guide defines a plurality of slots configured for at least a first proximal cut, a first sagittal cut, a second proximal cut, and a second sagittal cut to the tibia, the slots are configured to define a first medial-lateral cut length such that the first proximal cut is to a first single compartment of the tibia and are configured to define a second medial-lateral cut length such that the second proximal cut is to a second single compartment of the tibia.

In Example 22, the subject matter of Example 21 optionally includes wherein the second medial-lateral cut length is spaced from the first medial-lateral cut length by an intercondylar portion and the slots are configured to define the first sagittal cut on a first side of the intercondylar portion and a second sagittal cut on a second side of the intercondylar portion.

In Example 23, the subject matter of any one or more of Examples 18-22 optionally include further comprising inserting a pin or screw into the cut guide to limit one or both of the proximal cut and the sagittal cut.

In Example 24, the apparatuses or method of any one or any combination of Examples 1-23 can optionally be configured such that all elements or options recited are available to use or select from.

These and other examples and features of the present apparatuses and methods will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to devices and methods that can be used in a bi-cruciate preserving knee arthroplasty sometimes referred to as a bicompartmental knee replacement procedure. However, the techniques described are also applicable to a unicompartmental knee replacement procedure and/or a total knee replacement procedure (TKA). Examples of the bicompartmental knee replacement procedure can comprise a procedure that utilize two unicompartmental knee replacements and two femoral components, a procedure that utilizes a single (total) femoral component and two unicompartmental tibial components, a procedure that utilizes the single (total) femoral component and two unicompartmental bearings attached together by a U-shaped tibial tray and other types of knee replacement procedures. The disclosed devices include tibial cut guides having a mounting portion configured to couple with an alignment mechanism and a second portion connected to the mounting portion. According to some examples, the second portion can define a capture for a proximal cut and can have an aperture disposed adjacent a first end of the capture. According to further examples, the second portion can include a second capture for a sagittal cut.

Figure 1A:
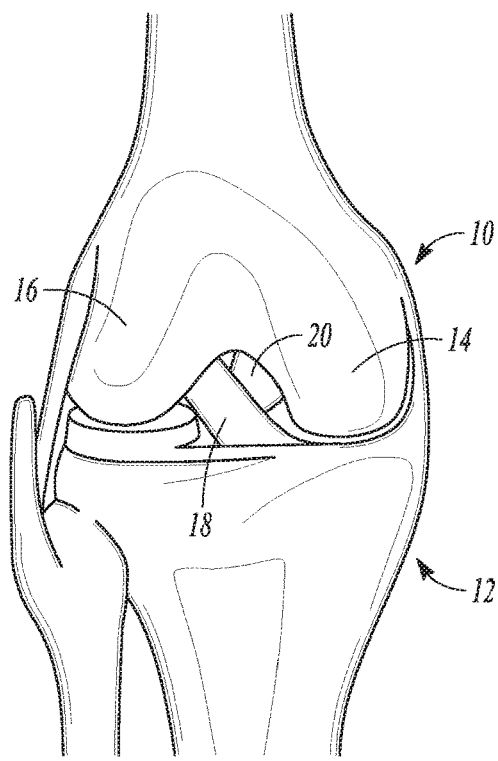
FIG. 1A is an anterior view of a natural femur and tibia according to an example of the present application.
Figure 1B:
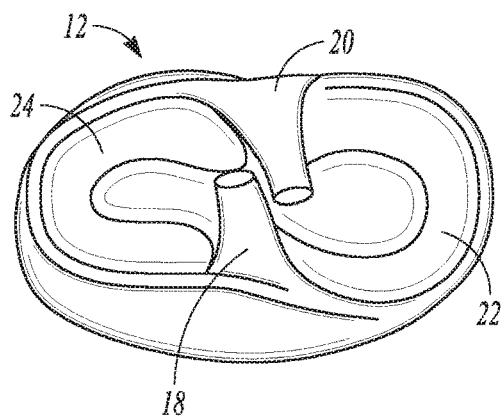
FIG. 1B is a top view of the tibia of FIG. 1A according to an example of the present application.

FIG. 1A illustrates a natural femur 10 and tibia 12. The femur 10 can include medial 14 and lateral 16 condyles at a distal end of the femur 10. Various ligaments can be attached to the femur 10 and/or the tibia 12. An anterior cruciate ligament (ACL) 18 can extend from an anterior side of the tibia 12 to the femur 10, and a posterior cruciate ligament (PCL) 20 can extend from a posterior side of the tibia 12 to the femur 10. FIG. 1B is a top view of the tibia 12 and further illustrates some of these ligaments as well as a medial meniscus 22 and a lateral meniscus 24 that are located between the tibia 12 and the medial 14 and lateral 16 condyles.

Figure 1C:
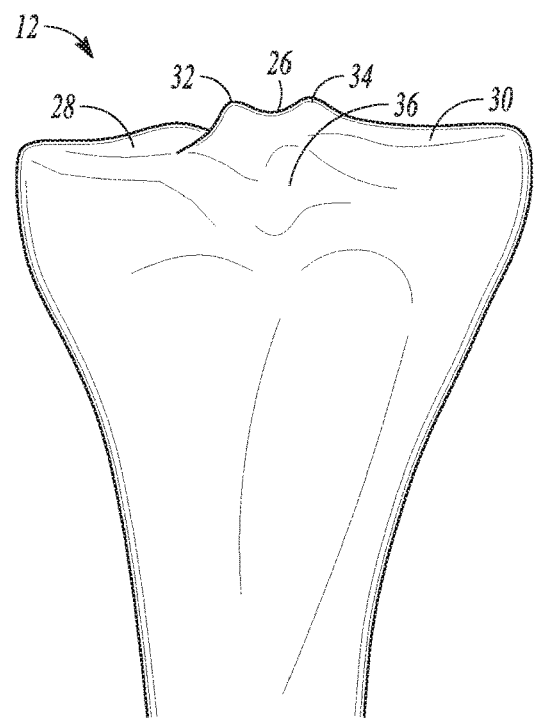
FIG. 1C is an anterior view of the tibia of FIGS. 1A and 1B, with the anatomical features shown in FIG. 1B removed according to an example of the present application.

FIG. 1C illustrates a posterior side view of the tibia 12 with the ligaments and other anatomical features shown in FIG. 1B removed. The tibia 12 can include an intercondylar eminence 26, which is a bony elevation or raised area between a medial articular surface 28 and a lateral articular surface 30 at a proximal end of the tibia 12. The intercondylar eminence 26 can include medial 32 and lateral 34 tubercles extending from the intercondylar eminence 26. The ACL 18 and PCL 20 are attached to the tibia 12 at locations anterior and posterior, respectively, to the intercondylar eminence 26. For reference, the PCL 20 is attached to the tibia 12 at location 36 on a posterior end of the tibia 12.

In a bicompartmental knee replacement procedure, the medial 14 and lateral 16 condyles of the femur 10 are resected. Similarly, the tibia 12 is resected to remove both of the medial articular surface 28 and the lateral articular surface 30 using a cutting apparatus such as those disclosed herein. More particularly, femoral cutting apparatuses can be utilized to remove portions of the femur 10 that would otherwise interface with either the medial articular surface 28 or the lateral articular surface 30. Prostheses would be implanted on the femur 10 and the tibia 12 providing for the replaced articular surfaces. Other portions of the knee, e.g., the intercondylar eminence 26, ACL 18, and PCL 20 can be maintained in the bicompartmental knee replacement procedure. In a unicompartmental knee replacement procedure, one the medial 14 and lateral 16 condyles of the femur 10 are resected and one of the medial articular surface 28 and the lateral articular surface 30 of the tibia 12 is resected. Such resection of the tibia 12 can be performed using a cutting apparatus as disclosed herein. Similar to the bicompartmental knee replacement procedure, the unicompartmental knee replacement procedure maintains portions of the knee such as the intercondylar eminence 26, ACL 18, etc. Similarly, a bicompartmental knee replacement procedure that would utilize a total femoral component and two unicompartmental tibial components or two tibial bearings and a U-shaped tibial tray can seek to maintain portions of the knee such as the intercondylar eminence 26.

As used herein, "proximal" refers to a direction generally toward the torso of a patient, and "distal" refers to the opposite direction of proximal, i.e., away from the torso of a patient. "Anterior" refers to front of the patient and "posterior" refers to the opposite direction of anterior back side of the patient or knee. In the context of cutting apparatus such as those disclosed herein, such directions correspond to the orientation of the apparatus when in use (i.e. when mounted to or adjacent the patient in an operable position to make desired resections), such that a proximal portion of the cutting apparatus is that portion which will ordinarily be closest to the torso of the patient, the anterior portion closest to the surgeon, the posterior portion generally closest to the anterior portion of the patient's knee, etc.

Figure 2:
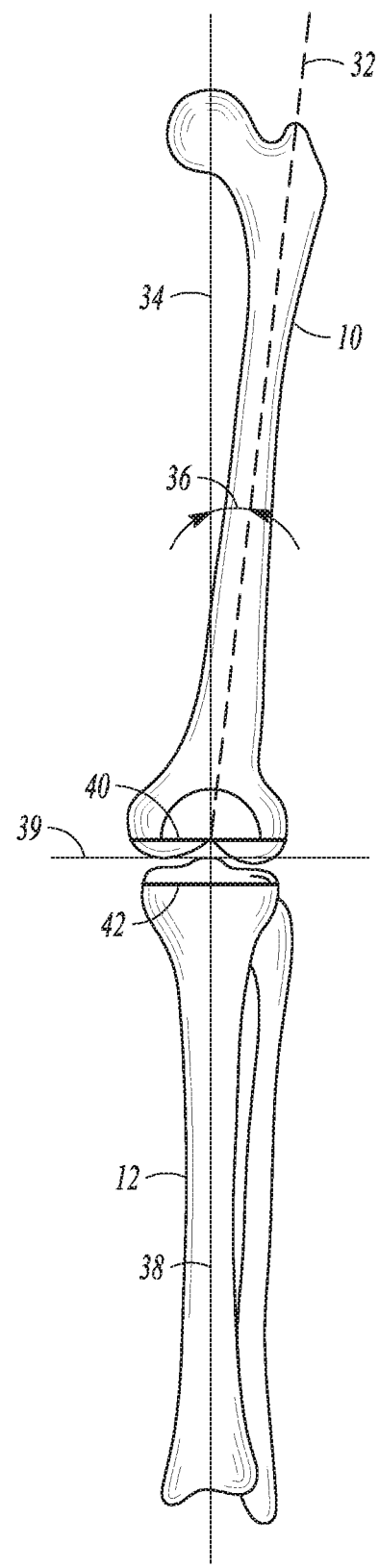
FIG. 2 is a front elevation view of a tibia and a femur showing axes of the knee joint according to an example of the present application.
Figure 3:
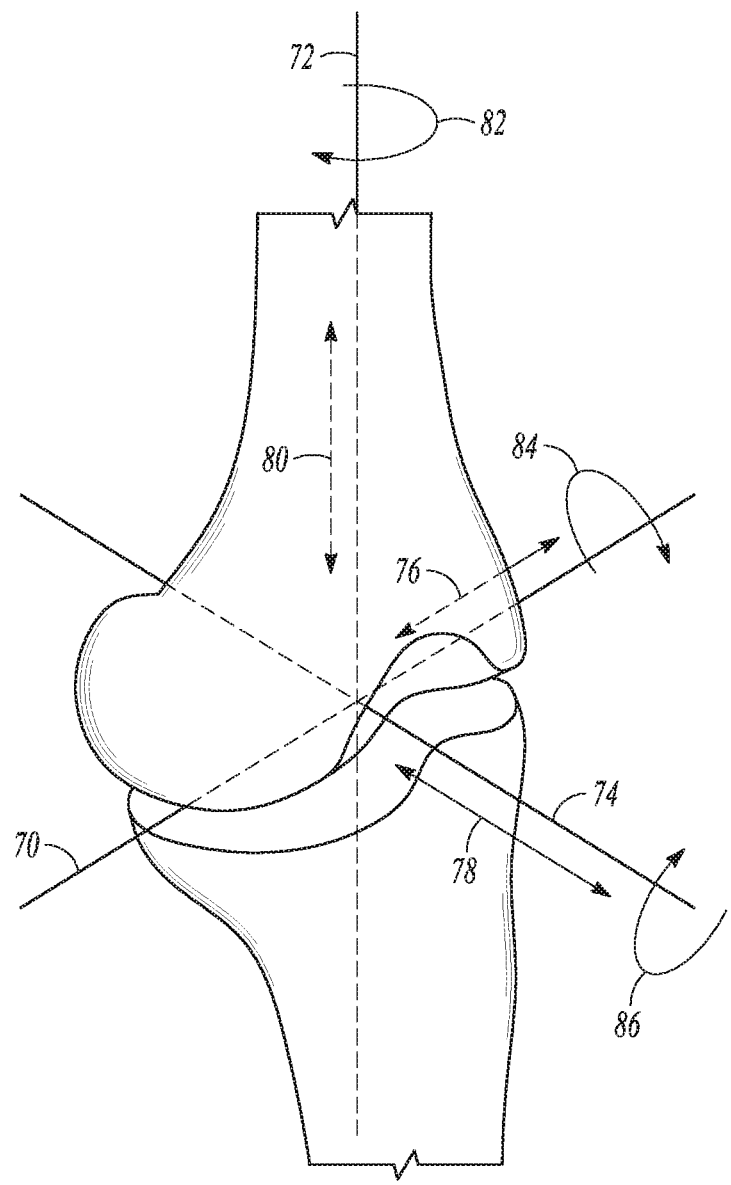
FIG. 3 is a perspective view of knee joint showing aspects of component positioning according to an example of the present application.

FIGS. 2-3 illustrate several aspects of implant orientation. FIG. 2 illustrates various axes of the lower limb in the frontal plane. Axes can be defined for each segment of the lower limb. For example, the femur 10 has an anatomic axis 32 coinciding generally with its intramedullary canal. It also has a mechanical axis 34, or load axis, running from the center of the femoral head to the center of the knee. The angle 36 between these two axes 32, 34 in the frontal plane varies within the patient population but is on the order of 4-9°. The two axes 32, 34 are approximately superimposed in the sagittal plane. Likewise, the tibia 12 has a mechanical axis 38 coinciding generally with its intramedullary canal. The mechanical axis 38 of the tibia 12 runs from the center of the knee to the center of the ankle. The transverse axis, or joint line 39, about which the knee flexes, is parallel to a line through the medial and lateral femoral condyles and parallel to the tibial plateau. Typically, the distal femur and proximal tibia are resected to be parallel to the joint line 39, and thus perpendicular to the mechanical axes 34, 38 as indicated at 40 and 42. The intersection of the femoral and tibial mechanical axes 34, 38 may subtend a small angle relative to one another. However, the angle can be small such that the axes 34, 38 are approximately collinear and may be treated as collinear for most purposes.

FIG. 3 depicts six aspects of component positioning relative to a coordinate system in which the x-axis 70 corresponds approximately to the joint line 39, the z-axis 72 corresponds approximately to the mechanical axes 34 and 38, and the y-axis 74 is normal to the other two. Position along each of these axes is depicted by arrows. Position along the x, y, and z axes determines the medial-lateral (dx) 76, anterior-posterior (dy) 78, and proximal-distal (dz) 80 positioning of components respectively. Rotation about each of these axes is also depicted by arrows. Rotation about the z-axis (rz) 82 corresponds anatomically to internal-external rotation of the femoral component, rotation about the x-axis (rx) 84 corresponds to flexion-extension rotation, and rotation about the y-axis (ry) 86 corresponds to varus/valgus rotation.

Figure 4:
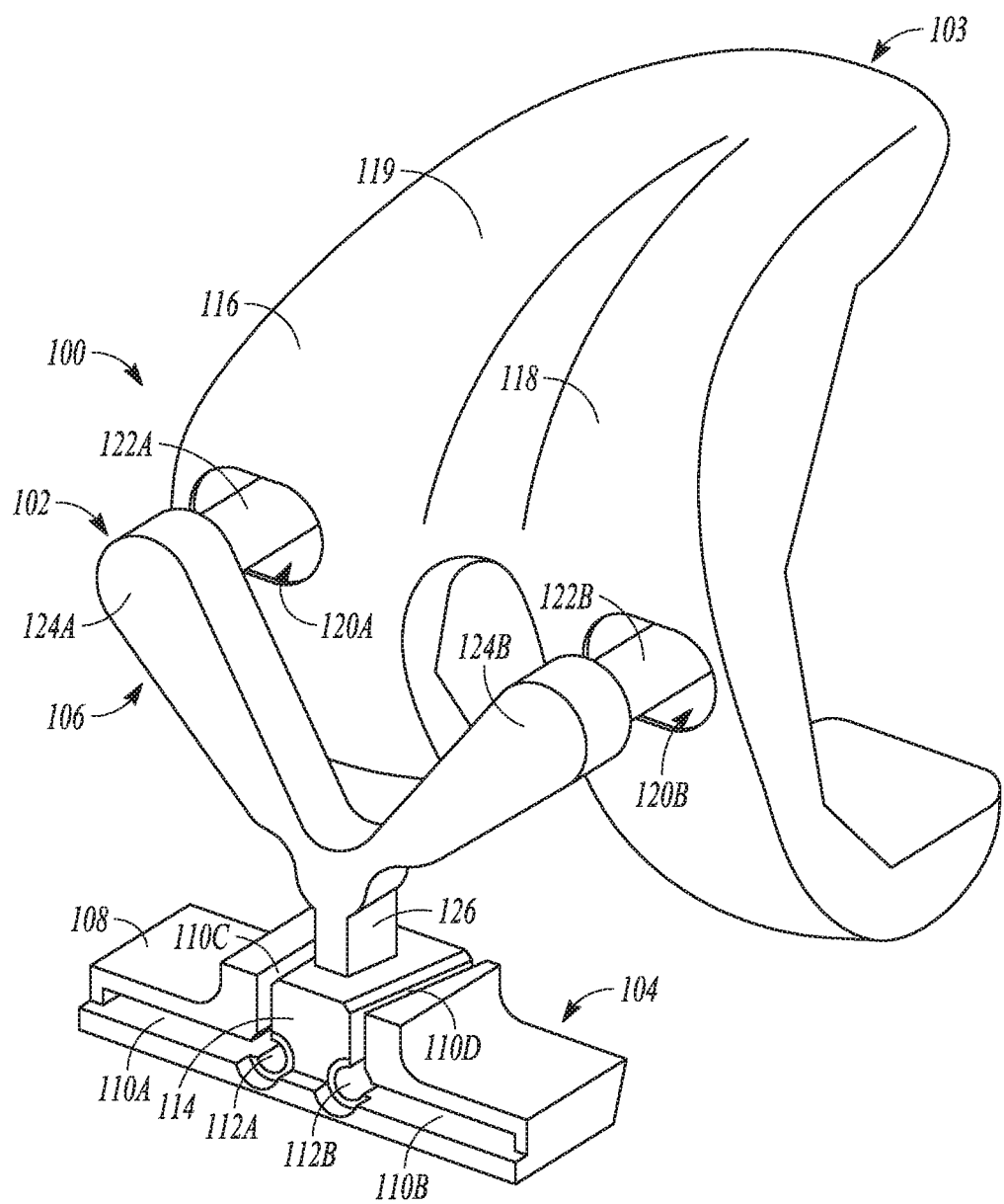
FIG. 4 is a perspective view of an assembly including a femoral component and a tibial cut guide with the tibial cut guide mounted to the femoral component according to an example of the present application.

FIG. 4 shows an assembly 100 of a tibial cut guide 102 and a femoral component 103 according to an example embodiment. As shown in FIG. 4, the tibial cut guide 102 can be connected to the femoral component 103 so as to be mounted thereto. The tibial guide 102 can include a mounting portion 104 and a cutting portion 106. The cutting portion 106 can include a body 108, slots 110A, 110B, 110C, and 110D, and apertures 112A and 112B. The body can include an intercondylar portion 114. The femoral component 103 can include a medial condyle 116, a lateral condyle 118, and connection features 120A and 120B.

Figure 5:
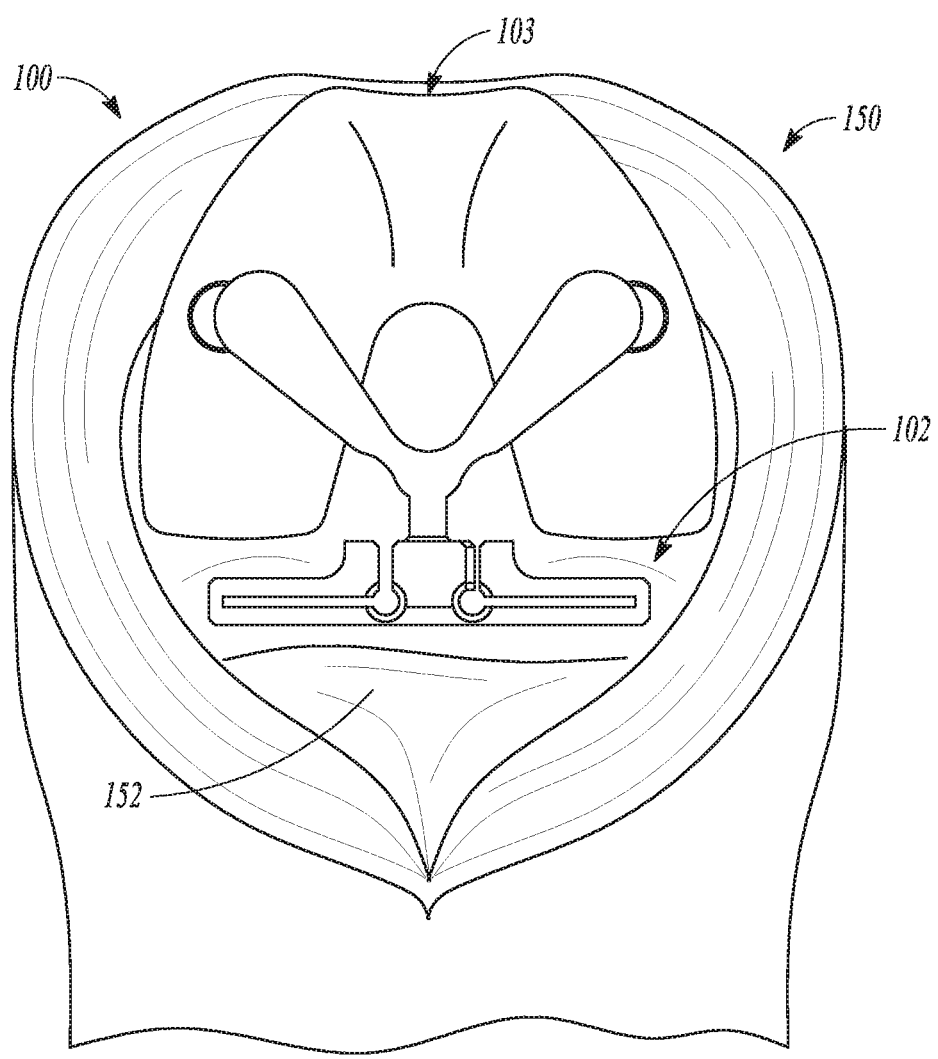
FIG. 5 is a perspective view of a knee of a patient having a cut guide mounted to the femoral component according to an example of the present application.

The tibial cut guide 102 of FIG. 5 can be configured for resecting one or both the medial and lateral compartments of the tibia. As such, the tibial cut guide 102 can be utilized to perform either the bicompartmental knee replacement procedure or the unicompartmental knee replacement procedure as described previously herein. With small modification (one single slot extending from substantially a lateral side to a medial side) the tibial cut guide can be used for a total knee replacement as well.

The mounting portion 104 can connect to the femoral component 103 at proximal ends thereof and can extend distally to connect with the cutting portion 106. A posterior surface of the cutting portion 106 can be configured to interface with an anterior portion of the tibia. The body 108 can comprise a frame that defines the slots 110A, 110B, 110C, and 110D. The slot 110A can be oriented generally medial-lateral for a first proximal cut. Similarly, the slot 110B can be spaced from the slot 110A and can be oriented generally medial-lateral for a second proximal cut. More particularly, the intercondylar portion 114 can space the slot 110A from the second slot 110B. The slot 110C can be configured for a first sagittal cut. The slot 110D can be spaced from the slot 110C by the intercondylar portion 114 and can be configured for a second sagittal cut. Thus, the tibial cut guide 102 can be configured such that first sagittal cut can be on a first side (e.g., a more lateral side) of the intercondylar portion 114 and the second sagittal cut on a second side (e.g., a more medial side) of the intercondylar portion 114.

As shown in the example of FIG. 4, the body 108 can additionally define apertures 112A and 112B disposed to either side of the intercondylar portion 114, respectively. The aperture 112A can be disposed between the slot 110C for the first sagittal cut and the slot 110A for the first proximal cut. Similarly, the aperture 112B can be disposed between the slot 110D for the second sagittal cut and the slot 110B for the second proximal cut. The aperture 112A can communicate with the slots 110A and 110C and the aperture 112B can communicate with the slots 110B and 110D. However, in other examples, the apertures 112A and 112B can be spaced from the slots 110A, 110B, 110C, and 110D by portions of the body 108. The aperture 112A can be disposed between the first of the one or more slots for the first sagittal cut and the second of the one or more slots for the first proximal cut.

According to some examples, the apertures 112A and 112B can be configured to receive one of a pin or screw (e.g., a stop or fixation component that separates the slots) therein. The screw or pin can provide for fixation of the cut guide 102 relative to the tibia. Additionally or alternatively, the screw or pin inserted in the aperture(s) 112A and 112B can provide a stop for the saw blade to protect the bone from over-resection. Additionally, fixation of the body 108 can be achieved by securing with pins/screws through the connection features.

For a bicompartmental knee replacement procedure, the slot 110A can be configured to define a first medial-lateral cut length and the slot 110B can be configured to define a second medial-lateral length. This can allow for the first and the second proximal cut to the tibia each of the first proximal cut and the second proximal cut to a different single (medial and/or lateral) compartment of the knee. In some cases the first medial-lateral cut length can differ from the second medial-lateral cut length.

According to the example of FIG. 4, the femoral component 103 can comprise a total femoral component that is a provisional (temporary) component with the medial condyle 116 spaced from the lateral condyle 118 by a patellar flange 119. The connection features 120A and 120B can be disposed in the medial condyle 116 and the lateral condyle 118, respectively. Additionally, the first arm 124A and the second arm 124B can be made adjustable about the intermediate portion 126 such that the mounting portion 104 can be attached to various sizes of femoral provisionals.

FIG. 4 illustrates the mounting portion 104, which can be configured to connect to the femoral component 103 with connection features 122A and 122B that are configured to couple with the connection features 120A and 120B, respectively. The connection of the mounting portion 104 to the femoral component 103 can mount the cutting portion 102 relative to the tibia. In the example of FIG. 4, the connection features 122A and 122B can comprise male features configured to couple with female features (connection features 120A and 120B). The connection features 122A and 122B can utilize tabs, treading, or other types of mechanical means known in the art to facilitate coupling with the connection features 120A and 120B.

According to the example of FIG. 4, the mounting portion 104 can include a first arm 124A having the first male connection feature 122A at an end thereof configured to connect with a first female connection feature 120A in the medial condyle 116. The mounting portion 104 additionally can include a second arm 124B having the second male connection feature 122B at an end thereof configured to connect with the second female connection feature 120B in the lateral condyle 118. The mounting portion 104 can have an intermediate portion 126 that can be connected to the first arm 124A and the second arm 124B at a proximal end portion thereof. The intermediate portion 126 can be connected to the cutting portion 106 at a distal end portion thereof.

FIG. 5 shows the assembly 100 of the tibial cut guide 102 and the femoral component 103 disposed in a knee joint 150 according to one example. The tibial cut guide 102 can be connected to mount to the femoral component 103 to interface with the anterior portion of a tibia 152.

Figure 6:
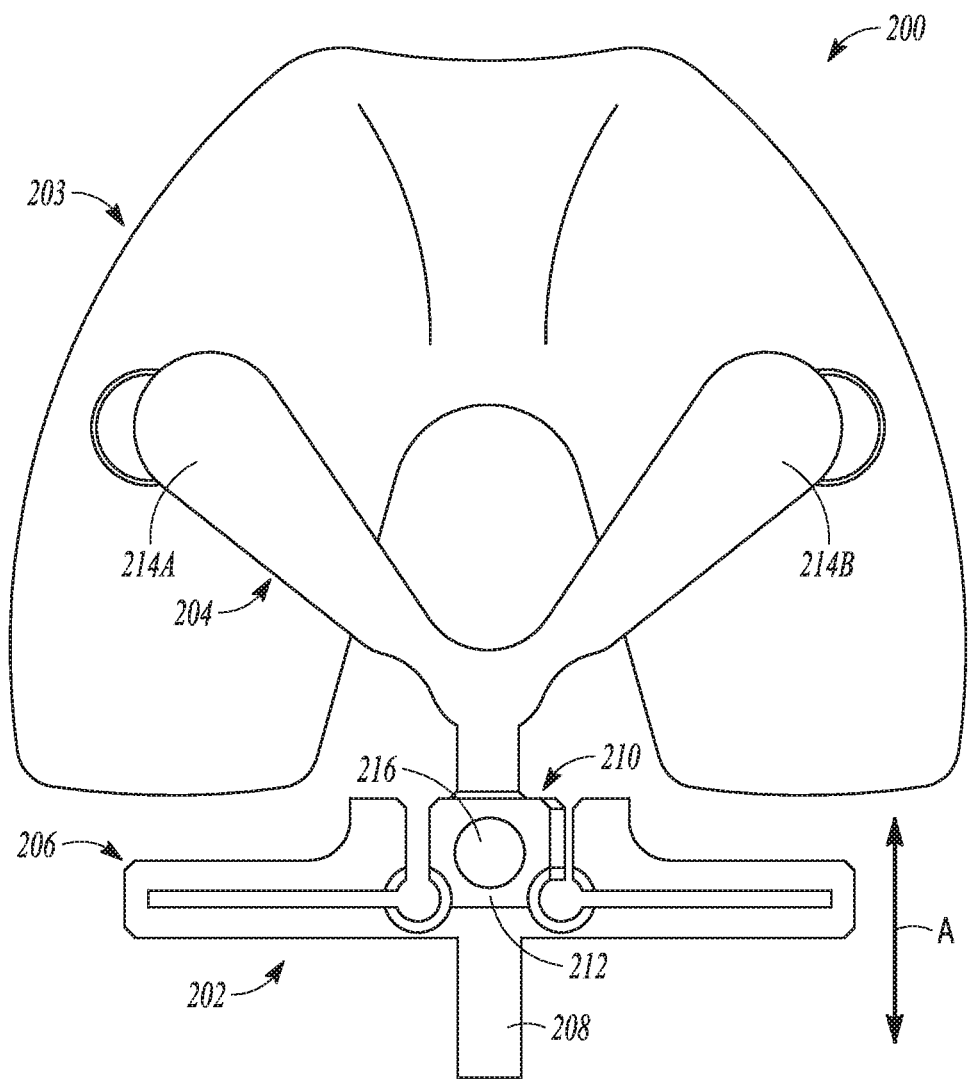
FIG. 6 is a plan view of another example of a tibial cut guide having an adjustment mechanism according to an example of the present application.

FIG. 6 shows an assembly 200 according to another example that can include a tibial cut guide 202 and a femoral component 203. The tibial cut guide 202 can couple to the femoral component 203 in the manner discussed previously with regard to the example of FIGS. 4 and 5. The tibial cut guide 202 can include a mounting portion 204 and a cutting portion 206.

Aspects of the mounting portion 204 (arms, connections) and the cutting portion 206 (slots, apertures, body, etc.) can be similar to those previously described with reference to FIGS. 4 and 5, and therefore, will not be discussed in great detail. The mounting portion 204 can additionally include an adjustment member 208. The cutting portion 206 can include an adjustment mechanism 210.

According to the example of FIG. 6, the adjustment mechanism 210 can be disposed at an intercondylar portion 212 of the cutting portion 206. The adjustment member 208 can extend generally in the proximal-distal direction from a junction with the arms 214A and 214B of the mounting portion 204.

The adjustment mechanism 210 can be configured to selectively couple with the adjustment member 208. More particularly, the adjustment mechanism 210 can receive the adjustment member 208, which can extend therethrough. The adjustment mechanism 210 can comprise a knob clamp 216 according to the example of FIG. 6. According to other examples, the adjustment member 208 can comprise another mechanical device that allows for selective locking, unlocking and adjustment (e.g., a ratchet, a gear, a clutch, a pin(s), or the like). The knob clamp 216 can be selectively loosened to allow for generally proximal-distal adjustment of the cutting portion 206 relative to the mounting portion 204 along the adjustment member 208. According to some examples, adjustment member 208 can be provided with teeth, recesses, or other mechanisms to facilitate selective locking with the adjustment mechanism 210. According to one example, the adjustment member 210 and adjustment member 208 can be configured to allow for between 0 mm and 15 mm of generally proximal-distal movement of the cutting portion 206 relative to the mounting portion 204 as indicated by arrow A.

Figure 7:
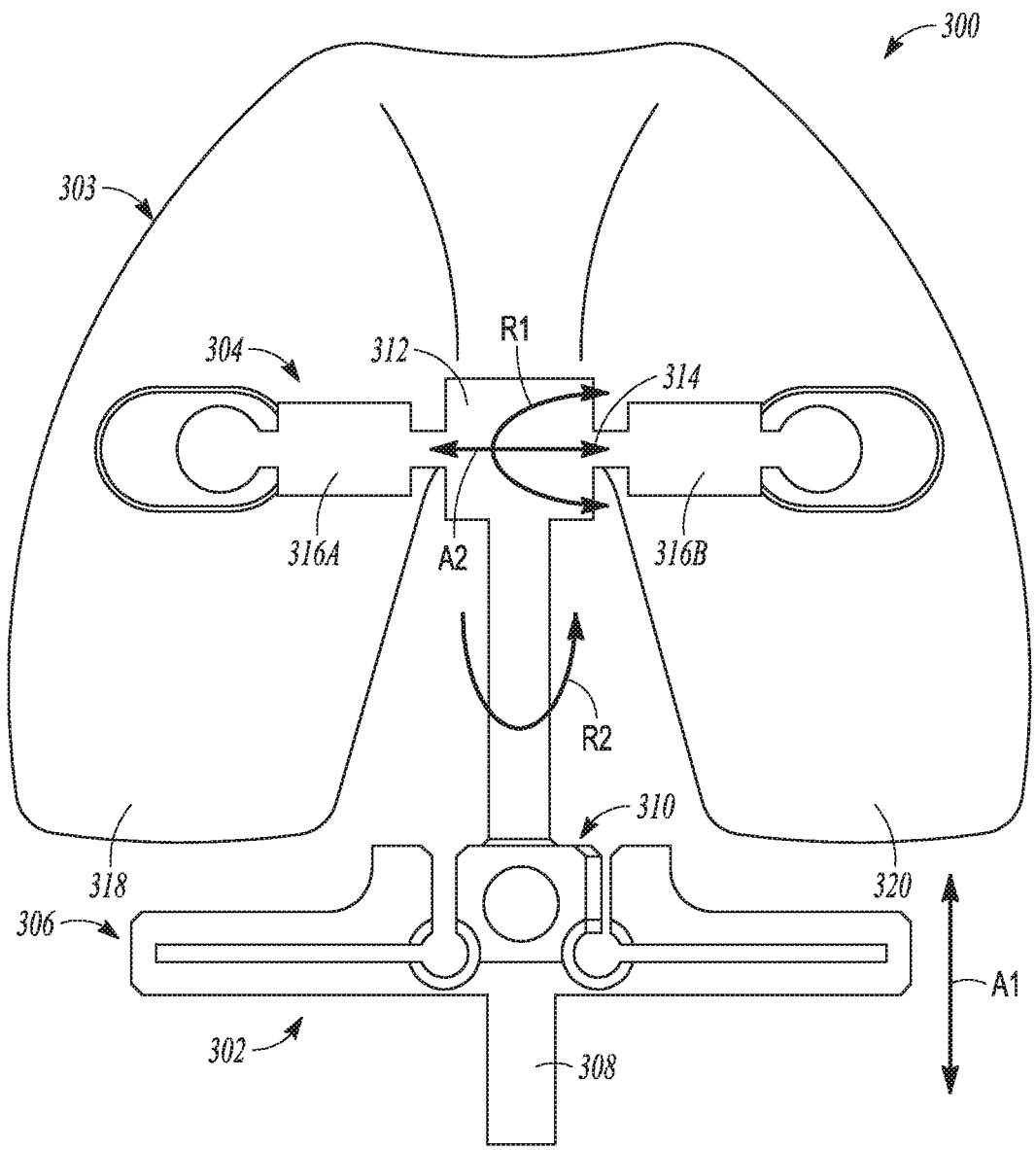
FIG. 7 is a plan view of yet another example of a tibial cut guide with a plurality of adjustment mechanisms according to an example of the present application.

FIG. 7 shows an assembly 300 according to another example that can include a tibial cut guide 302 and a femoral component 303. The tibial cut guide 302 can couple to the femoral component 303 in the manner discussed previously with regard to the example of FIGS. 4 and 5. The tibial cut guide 302 can include a mounting portion 304 and a cutting portion 306.

Aspects of the mounting portion 304 (connections) and the cutting portion 306 (slots, apertures, body, etc.) can be similar to those previously described with reference to FIGS. 4 and 5, and therefore, will not be discussed in great detail. The mounting portion 304 can additionally include an adjustment member 308 and the cutting portion 306 can include an adjustment mechanism 310 to facilitate generally proximal-distal adjustment (indicated by arrow $A_1$) of the cutting portion 306 relative to the mounting portion 304 as previously discussed in reference to the example of FIG. 6.

In the example of FIG. 7, the mounting portion 304 can further include a second adjustment mechanism 312, a second adjustment member 314 and stops 316A and 316B.

The second adjustment mechanism 312 can connect with the adjustment member 308 and can be selectively coupled with the adjustment mechanism 310. The second adjustment member 314 can extend generally transverse relative to the adjustment member 308 and can extend between a medial condyle 318 and a lateral condyle 320 of the femoral component 303. The stops 316A and 316B can be disposed on medial and lateral ends of the second adjustment member 314. The second adjustment mechanism 312 can be configured to receive the second adjustment member 314 and can allow for passage of the second adjustment member 314 therethrough.

The second adjustment mechanism 312 can be configured to selectively lock and unlock relative to the second adjustment member 314. This can allow for medial-lateral translation (indicated by arrow $A_2$) of the second adjustment mechanism 312 (and hence medial-lateral translation of the cutting portion 306 via the adjustment member 308) relative to the second adjustment member 314 and the medial and lateral condyles 318, 320 between the stops 316A and 316B. According to further examples, the stops 316A and 316B can be removed to allow for more unrestricted translation of the second adjustment mechanism 312 relative to the second adjustment member 314.

The second adjustment mechanism 312 can additionally be configured to facilitate rotation (indicated by arrows $R_1$ and $R_2$) and selective locking and unlocking of the adjustment member 308 (and hence rotation of the cutting portion 306). Such rotation can be about the z-axis (rz) 82 (FIG. 3) which corresponds anatomically to internal-external rotation of the femoral component and/or about the x-axis (rx) 84 (FIG. 3) which corresponds to flexion-extension rotation. The second adjustment mechanism 312 can utilize various mechanical features (knobs, screws, articulating joints, ratchets, or the like) to facilitate translation and/or rotation, locking and unlocking of the cutting portion 306 relative to the femoral component 303 and tibia (not shown). Thus, according to the example of FIG. 7, the adjustment mechanisms 310, 312 can adjust a position of the cutting portion 306 in one or more of rotation, a proximal-distal direction and a medial-lateral position. The second adjustment mechanism 312 can comprise a medial-lateral translation mechanism, a flexion-extension rotation mechanism and an internal-external rotation mechanism. The adjustment mechanism 310 can comprise a proximal-distal translation mechanism. Thus, the adjustment mechanisms 310, 312 can facilitate timely adjustment of the tibial cut guide 302 relative to femoral component 303 to accommodate physician preference, differences in patient anatomy and varying degree of flexion of the knee joint. Adjustment of the position of the tibial cut guide 302 relative to the femoral component 303 and the tibia 12 (FIGS. 1B and 1C) can be made with reference to at least one or more anatomical landmarks of the tibia 12 and/or the femur 10. The anatomical landmarks include one or more of the intercondylar eminence 26, a connection position of the ACL 18, a medial third of the tubercle at insertion of the PCL 20, and an intercondylar geometry of the femur 10.

Figure 8:
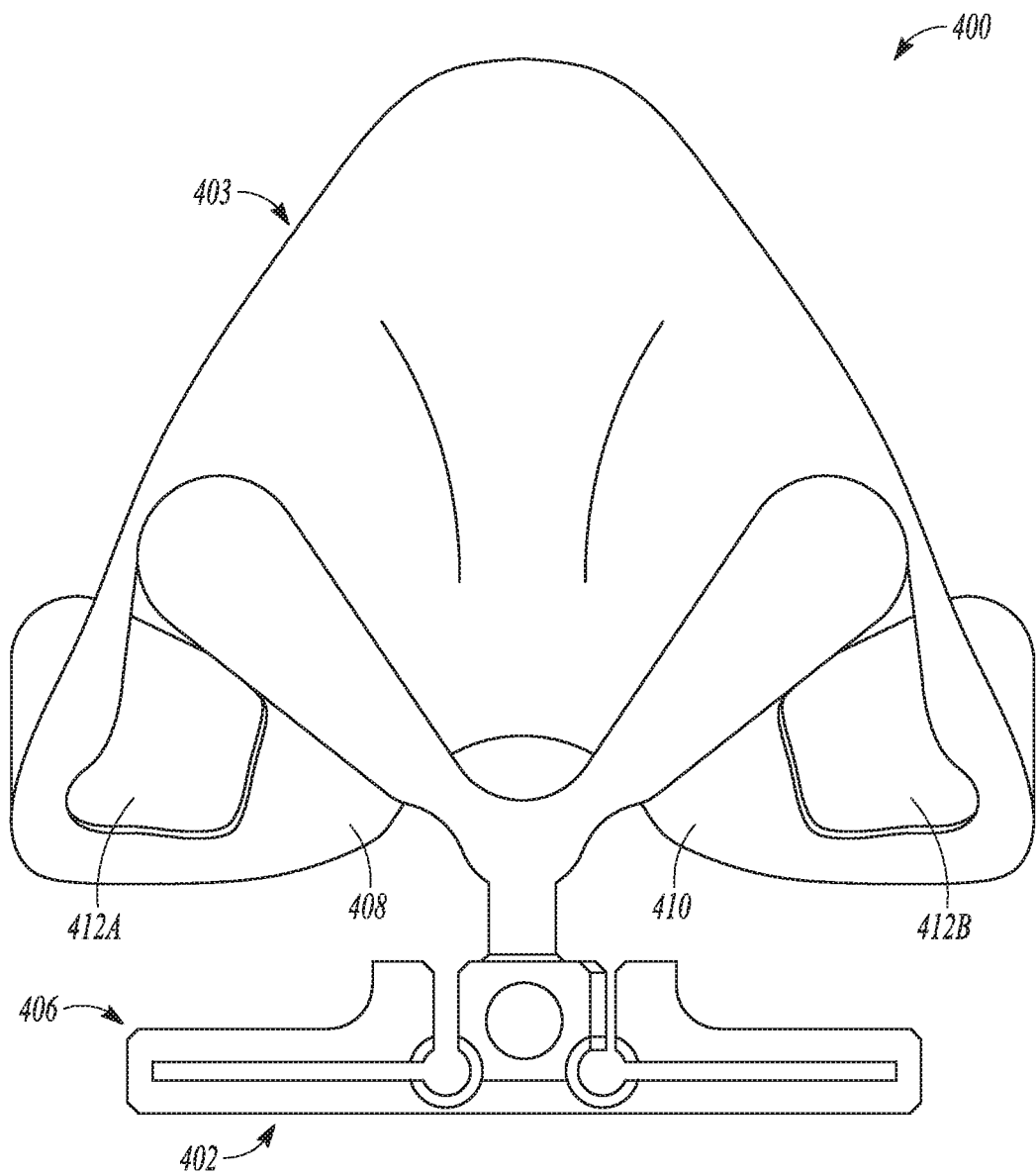
FIG. 8 is a plan view of the tibial cut guide with a second embodiment of the femoral component according to another example of the present application.

FIG. 8 shows an assembly 400 according to another example that can include a tibial cut guide 402 and a femoral component 403. The tibial cut guide 402 can be constructed in the manner discussed previously with regard to the example of FIGS. 4, 5, 6 and 7 and therefore, will not be discussed in great detail. The cut guide can include a mounting portion 404 and a cutting portion 406. The femoral component 403 includes a medial condyle 408, a lateral condyle 410, a first slot 412A and a second slot 412B.

The femoral component 403 can comprise a total femoral component that is a provisional component. The first slot 412A can be disposed in the medial condyle 408 and can be configured to receive a medial end of the mounting portion 404 therein. Similarly, the second slot 412B can be disposed in the lateral condyle 410 and can be configured to receive a lateral end of the mounting portion 404 therein. The first and second slots 412A, 412B can be configured to facilitate orientation of the cutting portion 406 in a desired position relative to the femoral component 403 and the tibia (not shown). As such, the first and second slots 412A, 412B can be used to accommodate physician preference, differences in patient anatomy (e.g., for resection depth) and varying degree of flexion of the knee joint.

Figure 9A:
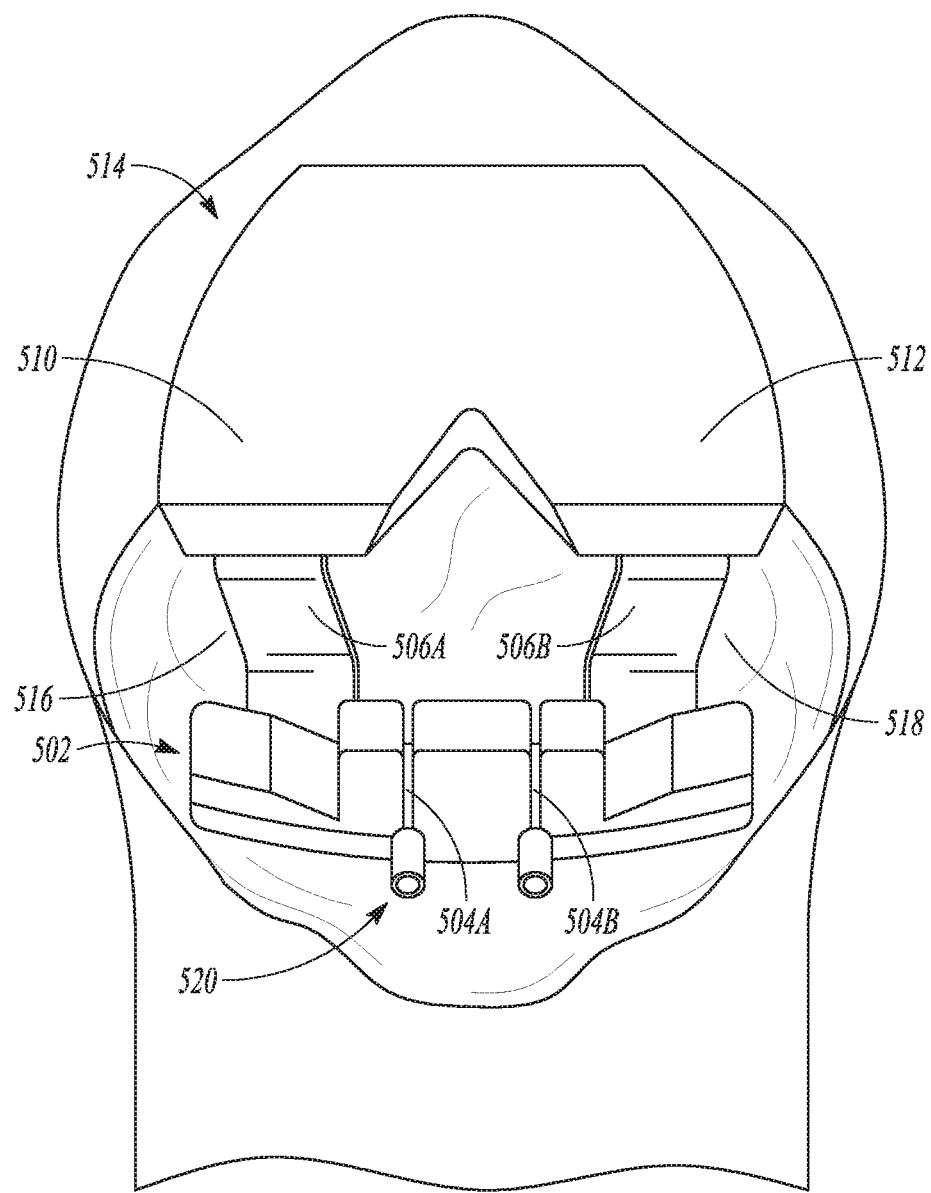
FIGS. 9A and 9B are perspective views of yet another example of the tibial cut guide which references the femur.
Figure 9B:
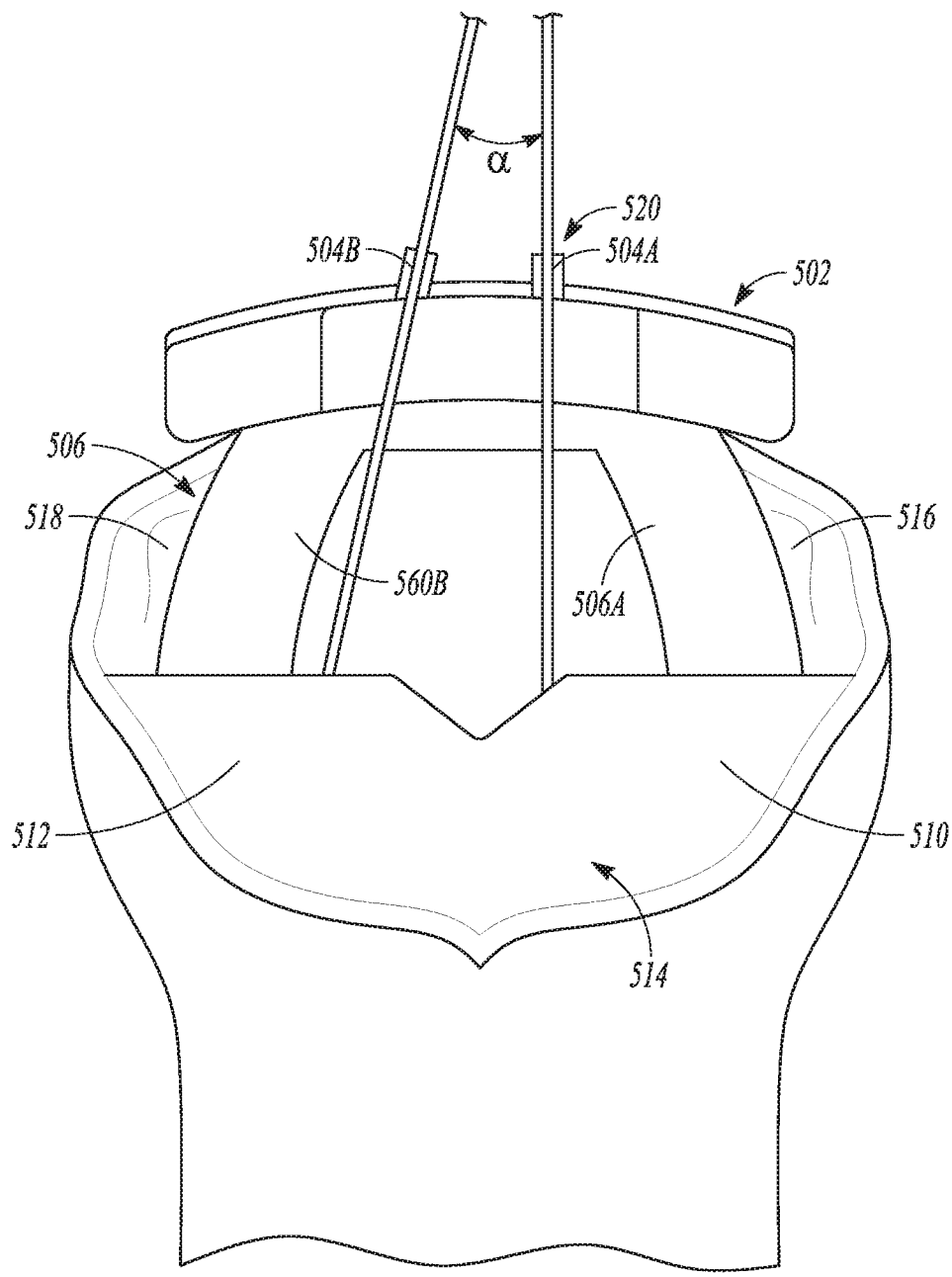

FIGS. 9A and 9B show a tibial cut guide 502 according to another example. The tibial cut guide 502 can be constructed to have slots including sagittal slots 504A and 504B arranged in the manner previously described in reference to the example FIGS. 4 and 5. The tibial cut guide 502 can additionally include a mounting portion 506 comprised of a first arm 506A and a second arm 506B. The first arm 506A and the second arm 506B can be configured to extend proximally and posteriorly from a cutting portion 508 of the tibial cut guide. The first and second arms 506A and 506B can be configured to position the apparatus relative to a medial condyle 510 and a lateral condyle 512 of the femur 514. According to some examples, the first arm 506A and the second arm 506B can rest upon the medial and lateral compartments 516, 518 of the tibia 520. FIG. 9B illustrates an example where a first sagittal cut defined by the slot 504A is canted at an acute angle α (as viewed from an elevated proximal position) relative to a second sagittal cut defined by the slot 504B.

Figure 10:
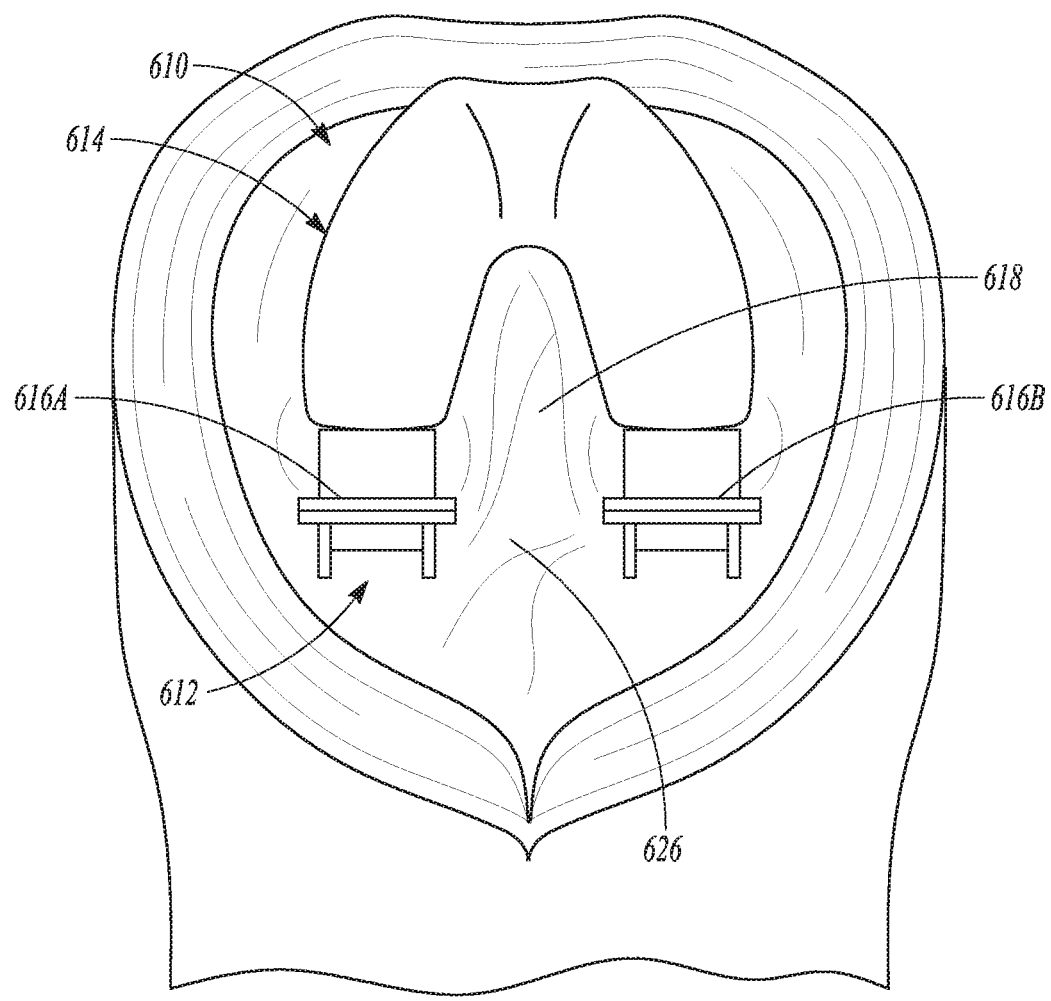
FIG. 10 is a perspective view of an example of provisional components utilized in a bi-cruciate retaining knee after resection of the tibial using any one of the tibial cut guide examples of the present application.

FIG. 10 shows a bicompartmental knee replacement procedure that can be performed using one or more of the tibia cut guides described herein. As shown, the medial and lateral condyles of the femur 610 are resected. Similarly, the tibia 612 is resected to remove both of the medial articular surface and the lateral articular surface using the tibial cut guides such as those disclosed herein. Prostheses (e.g., a total femoral prosthesis 614 and two unicompartmental tibial implants 616A and 606B) can are be implanted on the femur 610 and the tibia 612 providing for the replaced articular surfaces. Other portions of the knee, e.g., the intercondylar eminence 626, ACL 618, and PCL can be maintained in the bicompartmental knee replacement procedure due to the configuration of the tibial cut guides.

Figure 11:
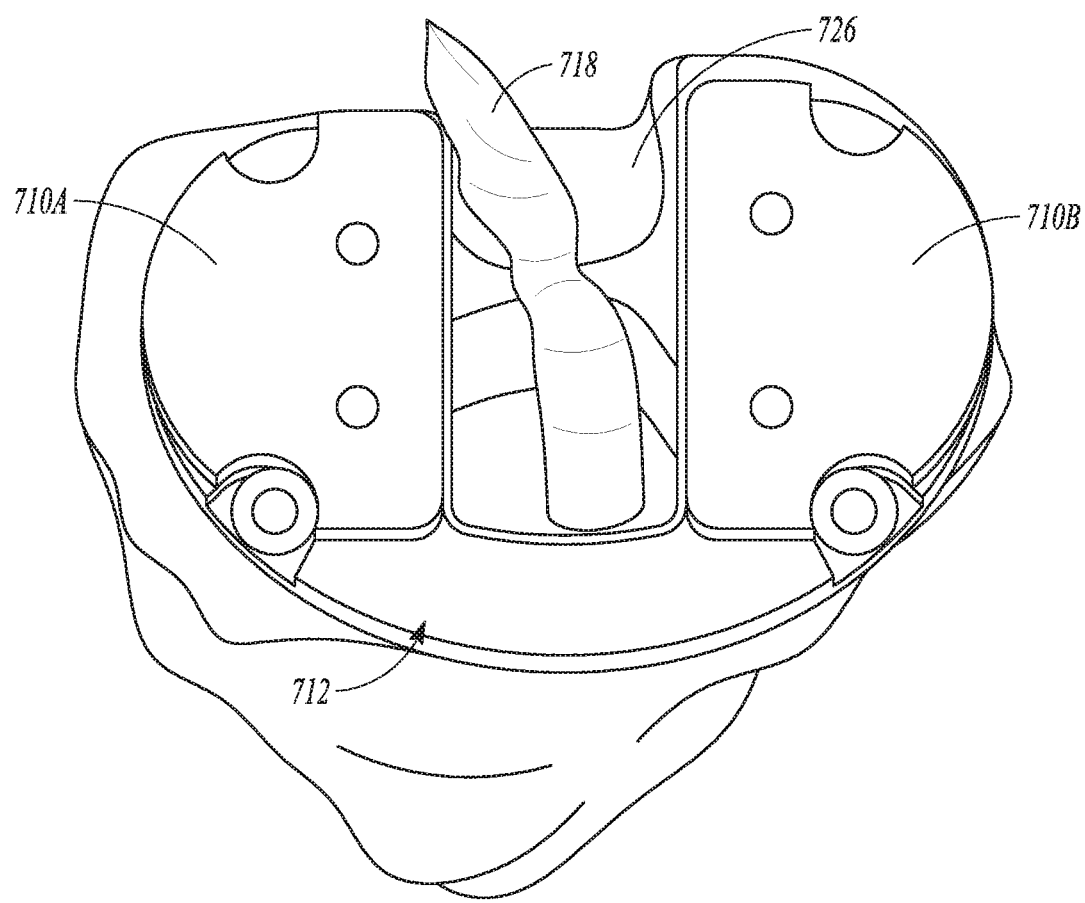
FIG. 11 is a plan view of a tibia with provisional components utilized in a bi-cruciate retaining knee after resection of the tibial using any one of the tibial cut guide examples of the present application.

FIG. 11 shows a bicompartmental knee replacement procedure that can utilize a total femoral component (such as the total femoral prosthesis 614 of FIG. 10), two tibial bearings 710A and 710B, and a U-shaped tibial tray 712 and seeks to maintain portions of the tibia 714 such as the intercondylar eminence 726 and the ACL 718. The bicompartmental arrangement of FIG. 11 can be performed using one or more of the tibia cut guides described herein.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplate examples in which only those elements shown or described are provided. Moreover, the present inventor also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A method of performing a tibial knee resection comprising:

connecting a cut guide to a femoral component mounted to a resected femur of a patient, the cut guide having slots configured to facilitate at least one of a first proximal cut and a first sagittal cut to a tibia, wherein the cut guide is connected to one or both of a medial condyle of the femoral component and a lateral condyle of the femoral component, and wherein the medial condyle and lateral condyle of the femoral component are configured to articulate with a tibial implant component; and resecting one or more compartments of the tibia by performing one or both of the proximal cut and the sagittal cut utilizing the cut guide.

2. The method of claim 1, further comprising adjusting a position of the cut guide relative to the femoral component and the tibia with reference to at least one or more anatomical landmarks of the tibia.

3. The method of claim 2, wherein the anatomical landmarks include one or more of an intercondylar eminence of the tibia, a connection position of an ACL with the tibia, a medial third of a tubercle at insertion of a PCL, and an intercondylar geometry of a femur.

4. The method of claim 1, wherein the slots are configured for at least the first proximal cut, the first sagittal cut, a second proximal cut, and a second sagittal cut to the tibia, the slots are configured to define a first medial-lateral cut length such that the first proximal cut is to a first single compartment of the tibia and are configured to define a second medial-lateral cut length such that the second proximal cut is to a second single compartment of the tibia.

5. The method of claim 4, wherein the second medial-lateral cut length is spaced from the first medial-lateral cut length by an intercondylar portion and the slots are configured to define the first sagittal cut on a first side of the intercondylar portion and a second sagittal cut on a second side of the intercondylar portion.

6. The method of claim 1, further comprising inserting a pin or screw into the cut guide to limit one or both of the first proximal cut and the first sagittal cut.

7. The method of claim 1, wherein the cut guide has a first portion configured to position the slots relative to the medial condyle of the femoral component and the lateral condyle of the femoral component.

8. The method of claim 7, wherein the cut guide further includes a second portion connected to the first portion and defining the slots.

9. The method of claim 7, wherein the first portion comprises:
a first arm having a first male connection feature configured to connect with a first female connection feature in the medial condyle of the femoral component;
a second arm having a second male connection feature configured to connect with a second female connection feature in the lateral condyle of the femoral component; and
an intermediate portion connected to the first arm and the second arm at a proximal end portion and connected to the second portion at a distal end portion.

10. The method of claim 1, wherein cut guide includes one or more adjustment mechanisms to adjust a position of the slots in one or more of rotation, a proximal-distal direction and a medial-lateral position.

11. The method of claim 10, wherein the one or more adjustment mechanisms comprise at least one of a proximal-distal translation mechanism, a medial-lateral translation mechanism, an extension plane rotation mechanism and an external rotation mechanism.

12. The method of claim 1, further comprising at least one aperture disposed between a first one of the slots for the first sagittal cut and a second one of the slots for the first proximal cut, the aperture is configured to receive one of a stop component or fixation component therein.

13. The method of claim 1, wherein the slots are configured to define a first medial-lateral cut length such that the first proximal cut is to a first single compartment of the tibia.

14. The method of claim 13, wherein the slots are configured to define a second medial-lateral cut length spaced from the first medial-lateral cut length by an intercondylar portion of the cut guide such that a second proximal cut is to a second single compartment of the tibia.

15. The method of claim 14, wherein the slots are configured to define the first sagittal cut on a first side of the intercondylar portion and a second sagittal cut on a second side of the intercondylar portion.

16. The method of claim 15, wherein the first sagittal cut is canted at an acute angle relative to the second sagittal cut.

17. A method of performing a tibial knee resection comprising:
connecting a cut guide to a femoral component mounted to a resected femur of a patient, the cut guide having slots configured to facilitate at least a first proximal cut and a first sagittal cut to a tibia, wherein the cut guide is connected to one or both of a medial condyle of the femoral component and a lateral condyle of the femoral component, and wherein the medial condyle and lateral condyle of the femoral component are configured to articulate with a tibial implant component;
adjusting a position of the slots relative to the femoral component in one or more of rotation, a proximal-distal direction and a medial-lateral position; and
resecting one or more compartments of the tibia by performing the first proximal cut and the first sagittal cut utilizing the cut guide.

18. The method of claim 17, wherein adjusting comprises using at least one of a proximal-distal translation mechanism, a medial-lateral translation mechanism, an extension plane rotation mechanism and an external rotation mechanism.

19. A method of performing a tibial knee resection comprising:
connecting a cut guide to a femoral component mounted to a resected femur of a patient, the cut guide having slots configured to facilitate at least a first sagittal cut and a second sagittal cut to a tibia, wherein the first sagittal cut is canted at an acute angle relative to a second sagittal cut, wherein the cut guide is connected to one or both of a medial condyle of the femoral component and a lateral condyle of the femoral component, and wherein the medial condyle and lateral condyle of the femoral component are configured to articulate with a tibial implant component; and
resecting one or more compartments of the tibia by performing at least the first sagittal cut and the second sagittal cut utilizing the cut guide.

20. The method of claim 19, wherein the slots are further configured to facilitate a first proximal cut and a second proximal cut of the tibia, and wherein the cut guide includes an intercondylar portion and the slots are configured to define the first sagittal cut and the first proximal cut on a first side of the intercondylar portion and the second sagittal cut and the second proximal cut on a second side of the intercondylar portion.

* * * * *